United States Patent
Bohets (10) Patent No.: US 9,645,107 B2
(45) Date of Patent: May 9, 2017

(54) CONDITIONING APPARATUS AND METHOD FOR ION-SELECTIVE ELECTRODE

(75) Inventor: Hugo Bohets, Antwerpen (BE)

(73) Assignee: Pion Inc., Billerica, MA (US)

( * ) Notice: Subject to any disclaimer, the term of this patent is extended or adjusted under 35 U.S.C. 154(b) by 993 days.

(21) Appl. No.: 13/583,267

(22) PCT Filed: Mar. 7, 2011

(86) PCT No.: PCT/EP2011/053367
§ 371 (c)(1),
(2), (4) Date: Oct. 19, 2012

(87) PCT Pub. No.: WO2011/110517
PCT Pub. Date: Sep. 15, 2011

(65) Prior Publication Data
US 2013/0199941 A1 Aug. 8, 2013

(30) Foreign Application Priority Data

Mar. 8, 2010 (GB) .................................. 1003720.8

(51) Int. Cl.
*G01N 27/333* (2006.01)
*G01N 27/416* (2006.01)

(52) U.S. Cl.
CPC ....... *G01N 27/333* (2013.01); *G01N 27/4163* (2013.01)

(58) Field of Classification Search
CPC .. G01N 27/333; G01N 27/414–27/417; G01N 27/4166; G01N 27/4167; G01N 27/301; G01N 27/302; G01N 13/00; G01N 33/15; G01N 2013/006
See application file for complete search history.

(56) References Cited

U.S. PATENT DOCUMENTS

| | | | |
|---|---|---|---|
| 2003/0057108 A1 | 3/2003 | Sridharan | |
| 2007/0231910 A1* | 10/2007 | DeGrandpre | G01N 31/16 436/56 |
| 2011/0247435 A1* | 10/2011 | Brinker et al. | 73/864.01 |
| 2012/0034704 A1* | 2/2012 | Hughes et al. | 436/178 |

FOREIGN PATENT DOCUMENTS

| | | |
|---|---|---|
| JP | 2005221271 A | 8/2005 |
| WO | 8502017 A1 | 5/1985 |

OTHER PUBLICATIONS

Fehér et al., Analyst, 99, 1974, 699-708.*
Moody et al., Analyst, 1988, 103-108.*
Rzewuska et al., Anal.Chem. 2008, 80, 321-327.*
International Preliminary Report on Patentability for PCT/EP2011/053367 dated Sep. 11, 2012.
Search Report for PCT/EP2011/053367 dated Jun. 8, 2011.
Bohets et al., "Development of in situ ion selective sensors for dissolution", Analytica Chimica Acta, vol. 581, No. 1, pp. 181-191, Jan. 2, 2007.

* cited by examiner

*Primary Examiner* — Gurpreet Kaur
(74) *Attorney, Agent, or Firm* — Dinsmore & Shohl LLP (57) ABSTRACT

Ion-selective electrodes (ISE's) optimized for analyte determinations and provides methods and apparatus for conditioning ion selective electrodes. The conditioning methods and apparatus are particularly useful for ISE's selective for, difficult to condition, less stable and temperature sensitive products, an are based on a concentration gradient and/or a short exposure to an increased temperature.

21 Claims, 8 Drawing Sheets

CONDITIONING APPARATUS AND METHOD FOR ION-SELECTIVE ELECTRODE

The present invention relates to the field of (universal) ion-selective electrodes (ISE's) optimised for analyte determinations and provides methods and apparatus for conditioning universal ion selective electrodes.

The conditioning methods and apparatus of the present invention are particularly useful for making universal ISE's selective for, difficult to condition, less stable and temperature sensitive products, and are based on a high concentration (gradient) and/or a (short) exposure to an increased temperature.

BACKGROUND TO THE INVENTION

For the determination of ions in solutions, use is frequently made of the potentiometric ion-selective electrode (Cammann, K., Die Arbeit mit Ionenselektiven Elektroden [Working with ion-selective electrodes], 2nd ed., Springer Verlag: Berlin, Heidelberg, N.Y., 1977). Ion-selective electrodes have widespread applications in the fields of biology, chemistry and medicine, the best known example being the pH-meter.

An ion-selective membrane is the key component of most potentiometric ion sensors. It establishes the preference with which the sensor responds to the analyte in the presence of various interfering ions from the sample. If ions can penetrate the boundary between two phases, then a electrochemical equilibrium will be reached, in which different potentials in the two phases are formed. Before ion selective electrodes are capable of making their intended measurement, they have to go through some form of conditioning. This is especially important for universal ion selective electrodes (H. Bohets Analytica chimica Acta 581(1):181-91, 2007 Jan. 2) where the selectivity determining ion-pair has to be formed in situ. The time it takes a universal sensor to become conditioned can vary from as little as a few hours to as long as a few weeks and is for example dependent on the analyte to be determined and the design of the sensor being used. For example, universal ion selective electrodes typically contain a plasticized PVC based ion-selective membrane. In said electrodes the conditioning time will be determined by the time it takes for the formation of the desired ion-pair (for example substituting K+ with the analyte ion), to take place, the consistency, i.e. electrochemical equilibrium of solute membrane interface, and the hydration of the ion-selective membrane.

For some analytes, the conditioning time may be unacceptably long, and although conditioning the electrodes at a higher temperature tends to accelerate the conditioning process, the latter is not always workable, such as for example when analyzing temperature sensitive components.

Another method to increase the conditioning speed is to work at higher concentration. It has been observed that this method is often limited by analyte solubility and post conditioning relaxation (drift not obtaining full sensitivity).

Combining elevated and high concentration will yield improved conditionings speed due to the synergy of both methods. High temperature will increase product solubility and membrane permeability, whereas high concentration will increase the probability of ion pair formation in the membrane. However, balancing of temperature and concentration versus decomposition and postconditioning relaxing is not obvious and product dependent. There is accordingly a need for a fast and simple procedure that allows the end user to optimize the conditioning method of universal ISE's in a straightforward procedure for a random analyte.

It has thus been an object of the present invention to provide an improved conditioning method addressing the aforementioned problems in a simple and more uniform procedure.

Depending on the level of method complexity different solutions are proposed.
1) Using High temperature typically for stable products
2) Using High concentration typically for well dissolving products
3) Using High temperature and high concentration typically for stable well dissolving products.
4) Using flash heating (sort period of time the component is heated) typically for less stable components.
5) Using flash heating and high concentration.
6) Using flash heating and high concentration gradient.
7) Using flash heating gradient and high concentration.
8) Using flash heating gradient and high concentration gradient.

Any of the above methods could be completed by a pulse of tensides present within the conditioning solution and/or relaxation of the ISE in an analyt solution (typically 100%) at measuring temperature.

This improved conditioning method is particularly useful in conditioning ISE's selective for difficult to condition, less stable and/or temperature sensitive products. By applying the conditioning solution at an elevated temperature and/or with a high concentration of the ion of interest, optionally with one or more of a gradually decreasing concentration of the ion of interest, flash heating and a pulse of tensides present within the conditioning solution, it has been observed that the conditioning procedure is less compound dependent. In other words, the more complex the conditioning procedure the more universal it gets. It is accordingly an objective of the present invention to provide a set of standardized 'active' conditioning procedures dependent on the characteristics of the analyte like, stability, solubility, temperature sensitivity and the like.

BRIEF DESCRIPTION OF THE DRAWINGS

With specific reference now to the figures in detail, it is stressed that the particulars shown are by way of example and for purposes of illustrative discussion of the different embodiments of the present invention only, and are presented in the cause of providing what is believed to be the most useful and readily description of the principles and conceptual aspects of the invention. In this regard no attempt is made to show structural details of the invention in more detail than is necessary for a fundamental understanding of the invention, the description taken with the drawings making apparent to those skilled in the art how the several forms of the invention may be embodied in practice.

FIG. 6. A: Shows the response of a passive conditioned ion-selective electrode and of an ion-selective electrode conditioned using the standard conditioning procedure for a stepwise addition of Loperamide. B: Is an enlarged image of FIG. 6A. Stability, and response time are visualized. The actively conditioned electrode shows discrete sharp steps.

FIG. 8. A: Shows the response of a tenside pulse conditioned ion-selective electrode and of an ion-selective electrode conditioned using the standard conditioning procedure for a stepwise addition of Cinnarizine. B: Is an enlarged image of FIG. 8A. Stability, and response time are visualized. The actively conditioned electrode shows discrete sharp steps.

FIG. 9. A: Shows the response of a standard conditioned ion-selective electrode, a tenside pulse conditioned ion-selective electrode and of an ion-selective electrode conditioned using the standard conditioning procedure for a stepwise addition of Loperamide. B: Is an enlarged image of FIG. 9A. Stability, and response time are visualized. The actively conditioned electrode shows discrete sharp steps. The tenside pulse conditioned and standard conditioned ion-selective electrode show similar discrete and sharp steps.

SUMMARY OF THE INVENTION

In a first embodiment the present invention provides a method of conditioning a universal ion selective electrode, said method comprising the step of contacting said ion-selective electrode with a flow of conditioning solution, wherein said conditioning solution is applied at an elevated temperature and/or with a concentration gradient of the conditioning solution; in particular with a high concentration of the analyte (i.e. of the ion of interest, hereinafter also referred to as the analyte of interest). The concentration gradient of the conditioning solution includes a decreasing concentration of the conditioning solution; in particular a decrease in the concentration of the analyte (ion of interest). For stable well dissolving products, the elevated temperature and high concentration are preferably combined, optionally with a gradually decreasing concentration of the ion of interest.

As used herein, a high concentration generally refers to a concentration of the ion of interest that is higher than the maximum concentration of the ion of interest one expects, i.e. one is willing to measure using the conditioned ISE. In the examples hereinafter, said maximum concentration (upper limit of the desired measuring range) is set to 100%.

In one embodiment of the conditioning methods of the present invention, and in particular for less stable components, the heat treatment of the conditioning solution is a flash treatment just prior to or during its exposure to the ion-selective electrode. Preferably the flash heated solution is continuously or intermittent refreshed at the sensor surface, old solution is discarded to waist or recycled in case of a closed system.

In an alternative embodiment, and in particular for less stable components, the conditioning solution is kept at a temperature of up to and about 37° C., and the concentration gradient of the conditioning solution is a pulse in the concentration of the tenside(s) present within the conditioning solution. Said pulse in tenside(s) concentration may optionally be combined with a gradient in the concentration of the analyte of interest; in particular with a decreasing concentration of the analyte of interest.

In a further aspect, the method(s) of the present invention may further comprise a gradual decrease in temperature of the conditioning solution. Said temperature is either continuously or discontinuously (e.g. stepwise) decreased.

As will become apparent from the examples hereinafter, in the methods of the present invention the concentration or temperature is continuously decreased or discontinuously decreased, such as for example in discrete steps or with a continuous gradient.

In a second embodiment the present invention provides an apparatus to perform the conditioning method as described hereinbefore, and characterized in that it comprises a (flow through) chamber, capable to accommodate and contact the ISE with the conditioning solution. As will be apparent to the skilled artisan, flow of the conditioning solution over the ion-selective electrode is meant to include laminar, turbulent and intermittent flows of the conditioning solution vis-a-vis the electrode, which may be achieved either by pumping (continuous or pulsated) the conditioning solution trough the flow chamber, and/or by agitation of the condition solution in the flow through chamber, such as for example by mixing or ultra sound.

The apparatus may further comprise means to achieve and maintain the aforementioned chamber at the desired temperature.

Since air bubbles may get trapped at the interface between the membrane of the ISE and the conditioning solution, the apparatus may in a particular embodiment, further comprise means to generate ultrasonic waves or mechanical agitation within the flow through chamber, to remove eventual air bubbles trapped at the interface between the membrane of the ISE and the conditioning solution As will be apparent to the skilled artisan, the flow through chamber may have any shape, and is preferably made of an inert material (such as for example glass), free of sharp edges, of a small volume and allows easy removal and observation of air bubbles.

In an even further embodiment the apparatus according to this invention, may further comprise means to feed the conditioning solution into said flow through chamber.

Also means to achieve and control the temperature of the conditioning solution, are optionally an integrated part of the conditioning apparatus of the present invention.

The apparatus may, further comprise means to achieve and control the concentration of the conditioning solution.

In a particular embodiment the apparatus according to the present invention, comprises;
  a conditioning chamber, capable to accommodate and contact the ISE with the conditioning solution;
  means to achieve and maintain the aforementioned chamber at the desired temperature;
  means to achieve and control the temperature of the conditioning solution; and
  means to achieve and control the concentration of the conditioning solution.

In a further embodiment the apparatus according to the present invention further comprises means to monitor the potential of the ISE at any stage of the conditioning procedure, and may include further means to apply a constant or oscillating potential on the ISE electrode.

The means to monitor the potential of the ISE, are in particular selected from means to determine any one or a combination of any of the following parameters; the endpoint of the senor conditioning, its calibration, and its validation. Said means allow determining one or more of the following; the drift of the ISE signal, the flow speed behaviour of the ISE signal, or the behaviour of the ISE upon concentration variations in the ion of interest.

It is accordingly a further objective of the present invention to provide the use of an apparatus as described hereinbefore, for conditioning a universal ion selective electrode and monitor the potential of the ISE at any stage of the conditioning procedure.

In one embodiment, of the aforementioned apparatus and/or use thereof, the conditioning process is monitored by determining the flow speed behaviour of the ISE signal.

In another embodiment, of the aforementioned apparatus and/or use thereof, the conditioning process is monitored by determining the drift of the ISE signal.

In an even further embodiment, of the aforementioned apparatus and/or use thereof, the conditioning process is monitored by determining the behaviour upon concentration variation of the ISE to validate and or calibrate the electrode.

DETAILED DESCRIPTION OF THE INVENTION

The present invention is based on the finding that the combination of a gradient flow-cell and a short exposure to an increased temperature of the conditioning solution results in an accelerated conditioning process of an ion-selective electrode and reduced relaxation times after conditioning.

It is accordingly a first objective of the present invention to provide a method of conditioning a universal ion selective electrode, said method comprising the step of contacting said ion-selective electrode with a continuous or discontinuous flow/exchange of conditioning solution, wherein said conditioning solution is applied with a concentration gradient of the conditioning solution; in particular at a high concentration of the analyt (i.e. the ion/analyte of interest) and/or at an elevated temperature. In a particular embodiment the conditioning solution is applied with a concentration gradient of the conditioning solution, including with a gradually decreasing concentration of the ion of interest.

Where straightforward speed conditioning is done at an elevated temperature in an excess solution, this has the disadvantage that prior to the actual use of the electrode an extended equilibration phase is still required. Again, to shorten this equilibration period one may be tempted to increase the equilibration temperature but given the dependency of the equilibrium on both the working temperature and concentration this does not always solve the problem.

It has now been found that when performing the conditioning and equilibration at an elevated temperature, with a gradual decrease in the concentration of the ion of interest results in ISE's that are (almost) immediately usable with a full signal and only limited drifting.

As will be apparent from the foregoing, the concentration gradient of the conditioning solution is preferably a variation in the concentration of the analyte of interest, but evidently may be combined with a variation in the concentration of one or more of the further components of the conditioning solution. Thus in an even further embodiment the concentration gradient of the conditioning solution is meant to include a variation in the concentration of one, two, three or more of the components of said conditioning solution, wherein said components are selected from the group consisting of; the analyt, buffer, electrolyte, tensides, solubility promoting agents, and phase transfer catalysts.

In a particular embodiment the concentration gradient is a variation in the concentration of the analyte (i.e. the ion/analyte of interest), optionally with a variation in the concentration of tenside(s). In a preferred embodiment the concentration gradient of the conditioning solution is either a variation in the concentration of the analyte (i.e. the ion/analyte of interest), in particular a decrease in the concentration of the analyte (i.e. the ion/analyte of interest); or a pulse in the concentration of tenside(s).

Said gradual decrease in concentration is optionally combined with a gradual decrease in temperature. In said embodiment the decrease in concentration is preferably, slightly leading on the decrease in temperature.

In a particular embodiment the 'active' conditioning procedure of the present invention includes a temperature gradient, that is optionally combined with a concentration gradient of the analyte (i.e. ion/analyte of interest) with.

Said temperature gradient typically involves;
starting the conditioning procedure at an elevated temperature from about 65° C. to about 90° C.; in particular from about 70° C. to about 90° C.;
keeping the flow cell at said elevated temperature for at least 30 minutes; in particular for between and about 2 hours to about 8 hours; more in particular for between and about 3 hours to about 4.5 hours; and
cooling the flow cell down (stepwise and/or continuously) to a temperature of about and below 37° C., over a period of between and about 15 min to about 8 hours; in particular for between and about 30 minutes to about 4 hours; more in particular for between and about 30 minutes to about 2 hours;

Said concentration gradient typically involves;
starting the conditioning procedure at an elevated concentration of the analyte (i.e. analyte/ion of interest) of about 2000% to about 1000%; in particular at about 1000%;
keeping the flow cell at said elevated concentration for at least 30 minutes; in particular for between and about 2 hours to about 8 hours; more in particular for between and about 3 hours to about 4.5 hours; and
lower the concentration of the analyte (stepwise and/or continuously) to a concentration of about and between 200% and 100%, over a period of between and about 15 min to about 8 hours; in particular for between and about 30 minutes to about 4 hours; more in particular for between and about 30 minutes to about 2 hours;

When combined the aforementioned temperature gradient and concentration gradient provide a conditioning procedure hereinafter referred to as the 'Standard' conditioning procedure according to the present invention.

In an alternative embodiment the conditioning procedure includes a change in concentration of the tenside(s) present within the conditioning solution.

Said change in tenside concentration typically involves;
starting the conditioning procedure in the absence of a tenside in the conditioning solution and at an analyte concentration of about 100%;
between and about 5 to 60 minutes; in particular between and about 10 to 20 minutes, after the start of the conditioning procedure a 10-20 minutes pulse of tenside solution added to the conditioning solution still comprising the analyte at the same concentration of about 100%; in a particular embodiment said tenside pulse is applied at a concentration of at least 5 weight percent (Wt. %); more in particular at least 10 Wt. %; even more in particular between and about 10 Wt. %-25 Wt. %; preferably about 10 Wt. %; and
keeping the conditioning solution and at an analyte concentration of about 100% for the remainder of the conditioning procedure.

This tenside pulse may be combined with either or both of the aforementioned temperature gradient and concentration gradient or alternatively, and in particular for temperature sensitive products with a conditioning solution that is kept constant at about 37° C. for at least 8 hours, in particular between and about 15 hours to 24 hours; more in particular between and about 18 hours to 21 hours. Conditioning procedures including the aforementioned tenside puls are hereinafter generally referred to as 'Tenside Puls' conditioning procedures.

It is accordingly a further objective of the present invention to provide a method of conditioning a universal ion selective electrode, said method comprising the step of contacting said ion-selective electrode with a continuous flow of conditioning solution, wherein said conditioning solution is applied at an elevated temperature and with a gradually decrease in temperature and concentration of the ion of interest.

In practice the concentration and/or temperature could be decreased in a discontinuous way or with a continuous gradient, including but not limited to an exponential decrease, a stepwise decrease or even an oscillating decrease in temperature and/or concentration.

Preferably with a continuous gradient, such as for example by using a gradient pump system to realize a gradient in the concentration of the conditioning solution and proportional-integral-derivative controller (PID controller) to realize a temperature gradient, such as for example found in plate-heaters.

In a further aspect the present invention provides an apparatus to perform the conditioning method of the present invention, and is characterized in that it comprises a chamber, hereinafter also referred to as a cell or conditioning chamber, capable to accommodate and contact the ISE with the conditioning solution. In its simplest form, the chamber consists of a recipient like a cup, that allows easy removal and change of the conditioning solution brought in contact with the ISE. Given the gradual decrease in concentration of the ion of interest, in a particular embodiment said chamber is a flow through cell with at least one entrance feeding the chamber with new conditioning solution and one exit clearing the conditioning solution after it has been in contact with the ISE. Through this continuous flow through of the heated conditioning solution there is only a short exposure of the analyt to the high temperature. This together with the continuous exposure to fresh product of the ISE (optionally at a decreasing concentration and or combined with a concentration additive profile (e.g. tensides)) was found to result in results in ISE's that are (almost) immediately usable with a full signal and only limited drifting.

Further means to achieve and maintain the aforementioned chamber at the desired temperature will also be present in the conditioning apparatus according to the present invention, and may for example include a proper insulation of the conditioning chamber in combination with, or alternatively using a heat exchanger such as a hot-water bath or a PID controller. In principle any means known for creating the desired temperature or temperature gradient can be used and include heating of the liquid and/or the conditioning chamber. Also direct heating of the sensor by direct contact, convection, or irradiation independently or in combination with flow cell/liquid heating, is an embodiment of the present invention. In one embodiment the heat treatment of the conditioning solution is a flash treatment just prior to or during its exposure to the ion-selective electrode, such as for example by limiting the heating of the conditioning solution to its flow through the heated conditioning chamber. Such flash treatment is particularly useful for less stable components.

The conditioning chamber is not made of a particular shape or size, but in order to assure a proper contact between the conditioning solution and the ISE, without interference in the equilibration process, the chamber is typically made of an inert material (such as for example glass), free of sharp edges, of a small volume and allows easy removal of air bubbles that may get trapped at interface between the ISE's membrane and the conditioning solution. The latter may for example be achieved through the application of ultrasonic waves or/and mechanical agitation within the conditioning chamber. Thus in a particular aspect the apparatus according to the present invention further comprises means to generate ultrasonic waves or/and mechanical agitation within the conditioning chamber.

Figure 3:
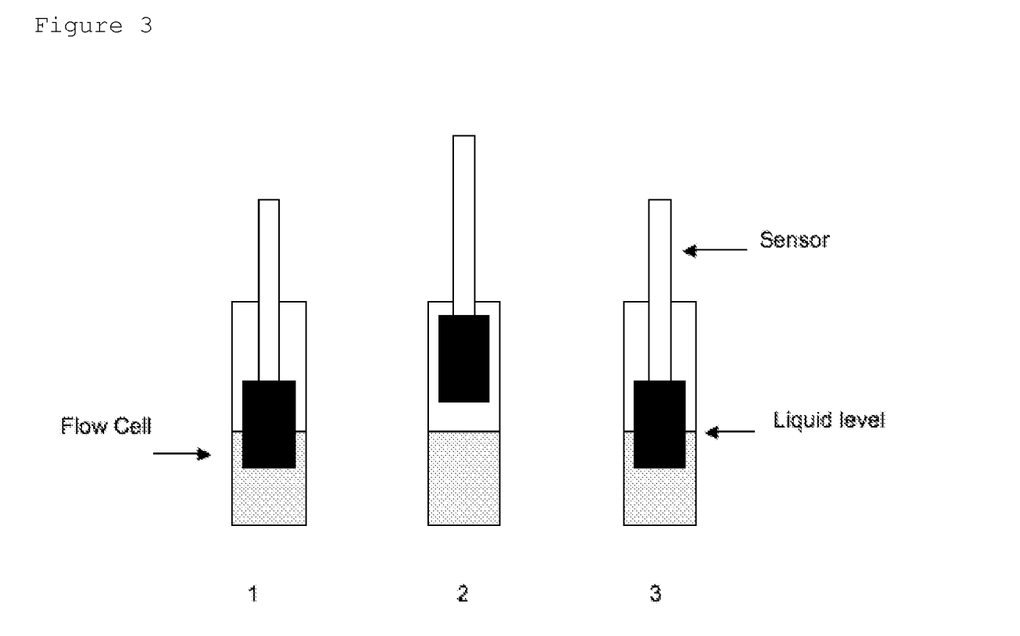
FIG. 3. A schematic drawing of a mechanical action for air bubble prevention/removal in/from the flow cell.

A specific embodiment of mechanical action is the process where the sensor is pulled out of the liquid and placed back in to the liquid (FIG. 3). This action can be performed by a mechanical device in a continuous or intermittent fashion. This action can for example be obtained by moving the (flow) cell, moving the sensor or both. Alternatively, the sensor is moved in and out the solution by varying (decrease & increase) the liquid level in the (flow) cell.

In a further aspect, the apparatus of the present invention comprises means to feed the conditioning solution into said conditioning chamber. Any means known to deliver a solution with a gradually decreasing concentration of the ion of interest, to the conditioning chamber can be used, and include for example a gradient pump system.

In a preferred embodiment the conditioning solution is brought at the desired concentration, rapidly brought to the desired temperature and delivered to temperature controlled conditioning chamber. In said embodiment the apparatus according to the present invention comprises;
- a conditioning chamber, capable to accommodate and contact the ISE with the conditioning solution;
- means to achieve and maintain the aforementioned chamber at the desired temperature;
- means to achieve and control the temperature of the conditioning solution; and
- means to achieve and control the concentration of the conditioning solution.

Another embodiment is an apparatus where the potential of the ISE is monitored during and after the conditioning cycle. Monitoring of the potential of the ISE at any stage of the conditioning procedure, includes any one or a combination of any of the following parameters; the endpoint of the sensor conditioning, its calibration and its validation. Said means to evaluate (monitor) the conditioning procedure typically allow to determine one or more of the following; the drift of the ISE signal, the flow speed behaviour of the ISE signal, or the behaviour of the ISE upon concentration variations in the ion of interest. A further refinement includes the evaluation of the conditioning process by (but not limiting to) the observation of the drift, changing the flow rate or doing a multi step calibration (step wise increment of concentration over time). Each of the foregoing parameters to monitor the potential of the ISE at any stage of the conditioning procedure will be performed using art known procedures, such as for example described in "A Beginners Guide to Ion-Selective Electrod Measurements"—Chris C Rundle BSc, PhD. (Nico2000 Ltd, London, UK.).

We found out that non or poor conditioned electrodes exhibit excessive drift, a dependence of the potential on the flow over the electrode and poor response to stepwise increased concentrations (deviation of the staircase profile which should be the response of such multi step calibration). The apparatus and/or user can use this data to adjust, repeat or end the conditioning process.

A further improvement of this setup will test the electrode by performing known discrete or continuous concentrations variations on the electrode surface which yield a sensor response that can be converted in to a validation and/or calibration report. The apparatus and/or user can use this data for analytic purpose or in case of poor performance to adjust, and/or repeat the conditioning process.

The conditioning process can further be improved by application of a constant or oscillating potential on the ISE electrode in order to facilitate the ion exchange. This electric conditioning process can be further improved by using a low or zero concentration of background ions.

This and other aspects of the apparatus according to the present invention will become apparent from the examples hereinafter.

EXAMPLES

1. Experimental Setup

Figure 1:
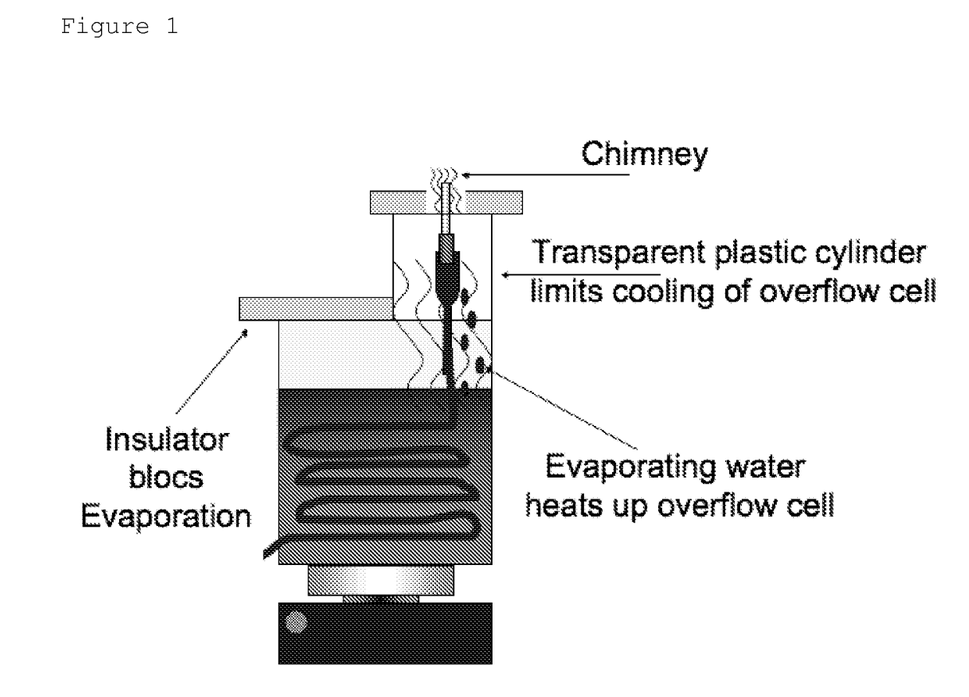
FIG. 1. A schematic drawing of an experimental setup of the conditioning chamber.

A schematic drawing of the experimental setup of the conditioning chamber is shown in FIG. 1. The ISE is positioned in an overflow cell that is kept at an elevated temperature and heat-controlled using a water bath. The water bath is insulated and surrounding the overflow cell in such a way that the evaporating water heats up the overflow cell. The overflow cell is fed with conditioning solution from underneath through tubing that has been led through the water bath.

As such the water bath functions as a heat exchanger to control the temperature of the conditioning solution.

Figure 4:
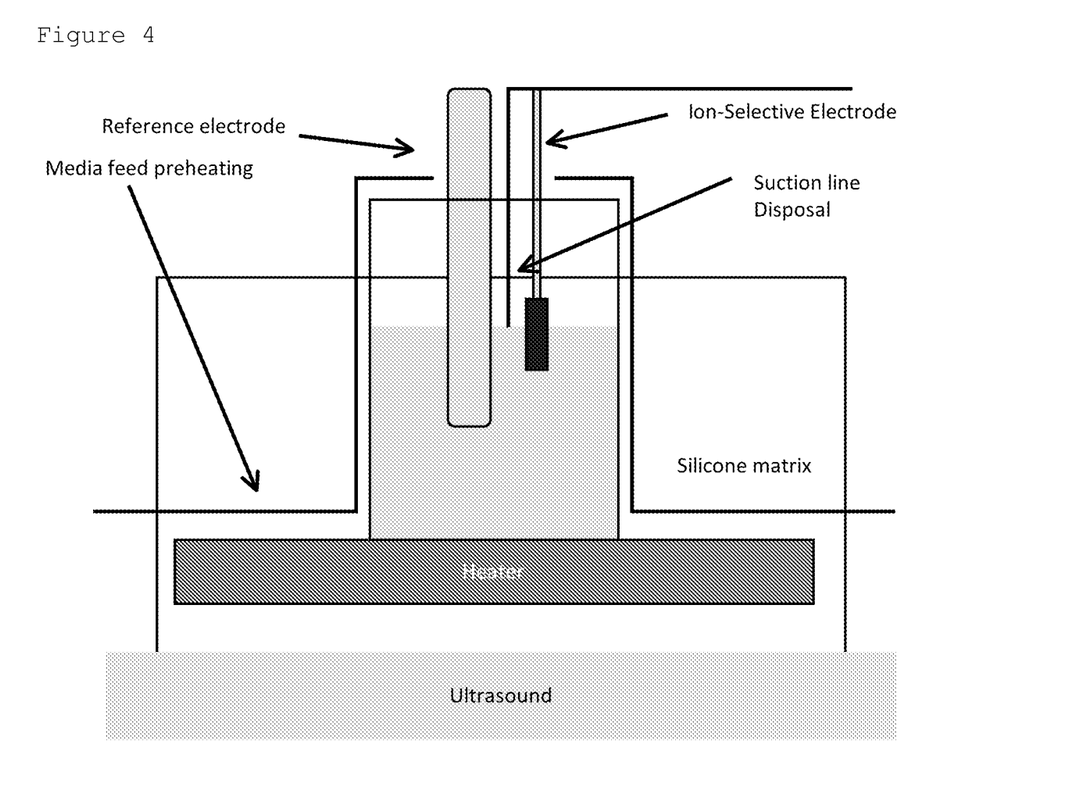
FIG. 4. A schematic drawing of an alternative setup of the conditioning chamber.

An alternative set-up of the conditioning chamber is shown in FIG. 4. In said instance, the temperature of the overflow cell is controlled through a block heater, and insulated using a silicone matrix. The overflow cell is fed with conditioning solution through tubing incorporated into the silicone matrix and excess conditioning solution is removed from the overflow cell by means of a suction line to the disposal. Optionally, the conditioning apparatus further includes an ultrasound generator beneath the silicone encapsulated block heater and flow cell, enabling the removal of air (air bubbles) from the overflow cell.

In said alternative set-up the temperature of the conditioning solution is controlled using a PID (Proportional Integral Derivative) controller.

2. Concentration Gradient at Elevated Temperature 2.1. Condition for Ranitidine Hydrochloride In a first experiment, using the experimental set-up of FIG. 1, the use of a concentration gradient at an elevated temperature was tested for the conditioning of an ion-selective electrode for Ranitidine hydrochloride (INN). This ion of interest is a histamine H2-receptor antagonist that inhibits stomach acid production. It is commonly used in treatment of peptic ulcer disease (PUD) and gastroesophageal reflux disease (GERD).
Conditioning Solution The conditioning solution is prepared in 10 mM. Acetate buffer at pH 5.0 and at room temperature.
Ion-Selective Electrode The Ion-Selective electrode consists of a gradient membrane electrode specifically developed for the dissolution testing of drugs and described in H. Bohets Analytica chimica Acta 581(1):181-91, 2007 Jan. 2.
Conditioning Procedure The concentration gradient is obtained using a dual pumping system or the gradual dilution system schematically represented in FIG. 2.

The conditioning process was performed using the following conditions;

Conditioning temperature is kept constant at ±70° C. start with the conditioning solution at 2000% for approximately 1 h 40 gradually converted into 200% over a period of 1 h 15 minutes (gradual conversion by the system shown in FIG. 2, using a 50 ml cylinder/2.5 ml in wide tube) Stop after 1 h 15 minutes on 200%

Result

Immediately after the aforementioned conditioning procedure, measuring a 100% solution at a temperature of 37° C., the ISE yields a full signal (tested after 40 minutes on 100% 37° C.)

The observed drifting (much better than classic high temperature conditioning) already disappears after 24 h of relaxation.

2.2. Concentration Variation Consisting of a Tenside Pulse at an Elevated Temperature The following experiments demonstrate the further benefits; in particular for active substances with a high log P, of a short tenside puls at the start of the conditioning procedure of the present invention.

In this procedure a short injection of Brij-35 at 80° C. was added to the initial standard conditioning procedure, and found to improve and accelerate the formation of the desired ion-pair.
Conditioning Solutions Conditioning for Cinnarizine:
100% Cinnarizine: 25 mg Cinnarizine/900 mL 0.01M HCl
10% Brij-35: 1 g Brij-35/10 mL 100% Cinnarizine
Conditioning for Loperamide:
100% Loperamide: 2 mg Loperamide/900 mL 0.01M HCl
10% Brij-35: 1 g Brij-35/10 mL 100% Loperamide
Conditioning for Amitriptyline:
100% Amitriptyline: 25 mg Amitriptyline/900 mL 0.1M HCl
10% Brij-35: 1 g Brij-35/10 mL 100% Amitriptyline
Conditioning for Diphenhydramine:
100% Diphenhydramine: 50 mg Diphenhydramine/900 mL 0.01M HCl
10% Brij-35: 1 g Brij-35/10 mL 100% Diphenhydramine
Conditioning for Meclizinedihydrochloride:
100% meclizinedihydrochloride: 22.5 mg meclizinedihydrochloride/900 mL 0.01M HCl
10% Brij-35: 1 g Brij-35/10 mL 100% meclizinedihydrochloride
Ion-Selective Electrode The Ion-Selective electrode consists of a gradient membrane electrode specifically developed for the dissolution testing of drugs and described in H. Bohets Analytica chimica Acta 581(1):181-91, 2007 Jan. 2.
Conditioning Procedure The concentration gradient is obtained using a dual pumping system or the gradual dilution system schematically represented in FIG. 2.

The temperature of the fed conditioning solutions was controlled using an external temperature control unit such as for example using a PID control unit.

Figure 7A:
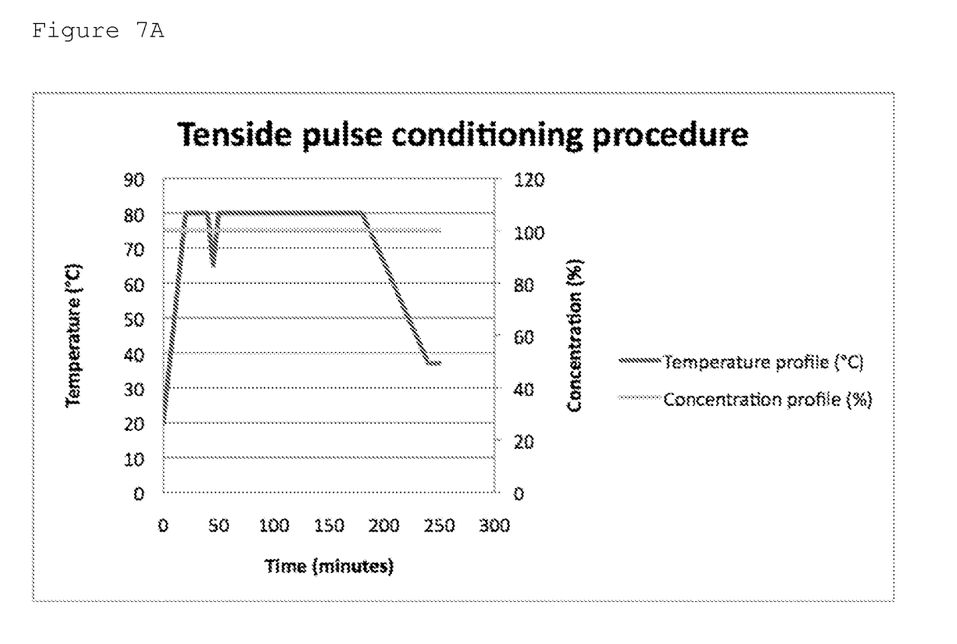
FIGS. 7A & B. Shows two alternatives of the temperature and concentration profile of a tenside pulse conditioning procedure.

But for Amitriptyline, the conditioning process was performed using the following conditions (FIG. 7A);

Conditioning temperature is kept at ±80° C. for about 20 minutes.

A one time injection of 10% Brij-35 mixed with the 100% conditioning solution is executed.

After 3 h at 80° C., the temperature cools down at 37° C. in 1 h still in 100% solution.

The electrode is kept for about 20 hours at 37° C./100% solution before testing.

Figure 7B:
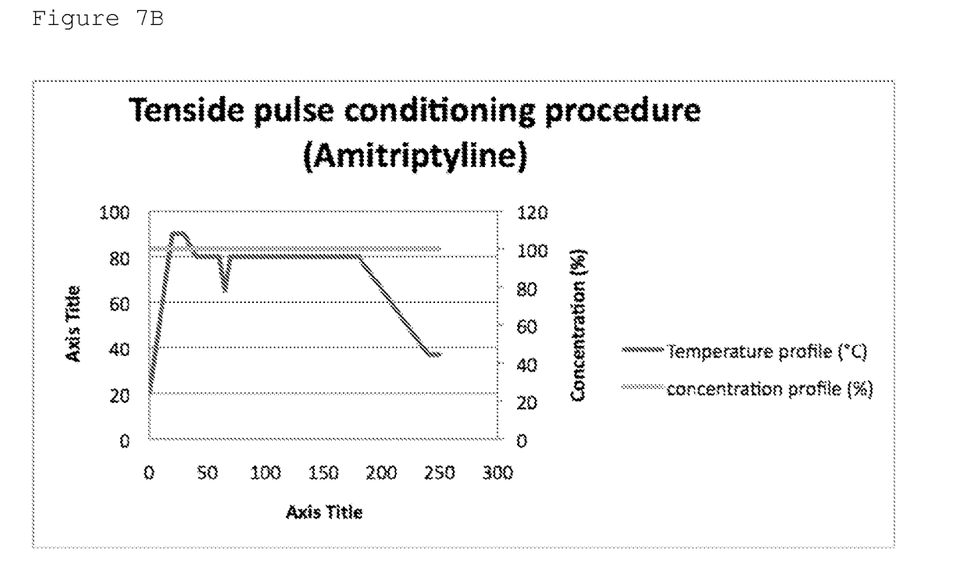

For Amitriptyline, the conditioning process was performed using the following conditions (FIG. 7B);

Conditioning temperature is kept at ±90° C. for about 10 minutes.

When a temperature of 80° C. is achieved for about 20 minutes a onetime injection of 10% Brij-35 mixed with the 100% conditioning solution is executed.

After 3 h at 80° C., the temperature cools down at 37° C. in 1 h still in 100% solution.

The electrode is kept for about 20 hours at 37° C./100% solution before testing.

Result

Figure 8A:
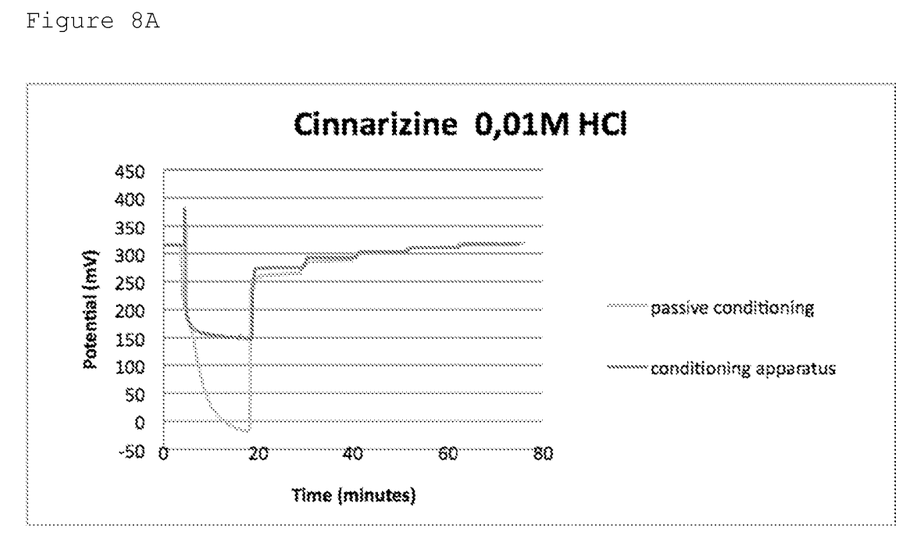
Figure 8B:
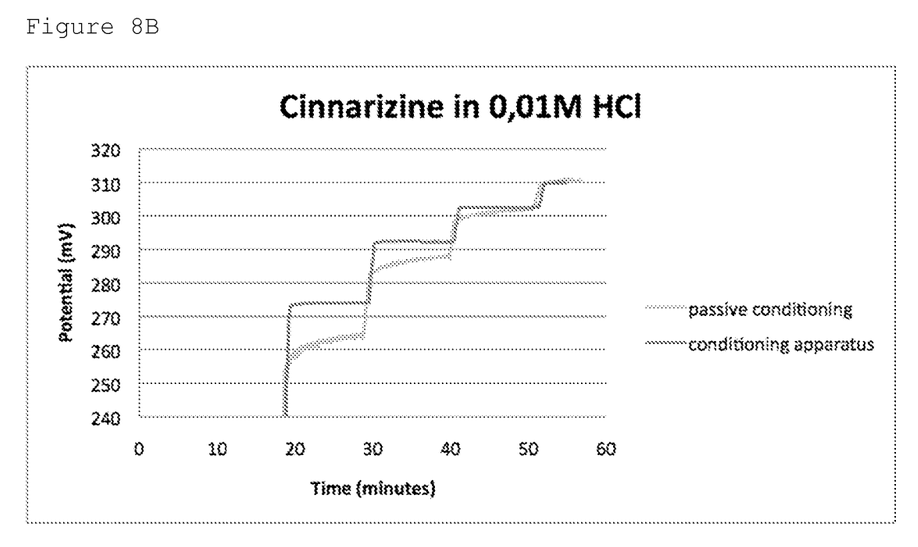

Immediately after the aforementioned conditioning procedure, measuring a 100% solution at a temperature of 37° C., the ISE yields a quick responding and full signal that is more stable than the signal of an passive conditioned electrode that had been exposed at a 100% solution for the same time range (FIG. 8A/8B), when exposed to a stepwise addition of Cinnarizine.

Electrodes that were treated at high temperature and with addition of a tenside (Brij-35) showed much better results than passive conditioned electrodes exposed to the drug (100% solution/37° C.) in the same timeframe. The electrodes showed a quick response, were more stable (less noisy signal) and less sensitive to the formation of air bubbles during measurements.

3. Concentration Gradient and Temperature Gradient 3.1. Concentration Gradient and Temperature Gradient The ion of interest is Ranitidine hydrochloride (INN) a histamine H2-receptor antagonist that inhibits stomach acid production. It is commonly used in treatment of peptic ulcer disease (PUD) and gastroesophageal reflux disease (GERD).

The conditioning solution is prepared in 1 mM HCl at a room temperature.

The Ion-Selective electrode consists of a gradient membrane electrode specifically developed for the dissolution testing of drugs and described in H. Bohets Analytica chimica Acta 581(1):181-91, 2007 Jan. 2.

Figure 2:
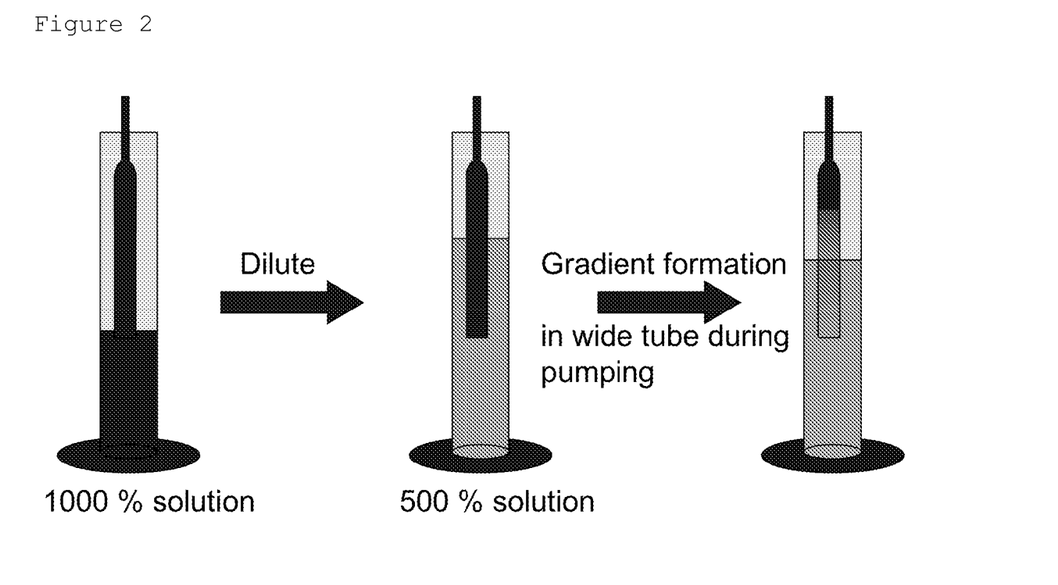
FIG. 2. A schematic drawing of a gradual dilution system

The concentration gradient is obtained using a dual pumping system or the gradual dilution system schematically represented in FIG. 2.

The temperature gradient is obtained through passive cooling of the water bath.

The conditioning process was performed using the following conditions;

Temperature conditioning +−80° C.

All steps (gradual conversion by system above 50 ml cylinder/2.5 ml in wide tube (FIG. 2))

start 2000% for approximately 42 minutes set on 400% for approximately 52 minutes Set on 120% for approximately 1 hour 20 minutes (slightly cooler)

Immediately after the aforementioned conditioning procedure, measuring a 100% solution at a temperature of 37° C., the ISE yields a full signal (tested after 40 minutes on 100% 37° C.) with a reasonable drifting of only about 12 mV over 24 h. The observed drifting (much better than classic high temperature conditioning) already disappears after 24 h of relaxation.

3.2. Condition for Loperamide

In a second experiment, using the experimental set-up of FIG. 4, the use of a concentration gradient at an elevated temperature in combination with a temperature gradient was tested for the conditioning of an ion-selective electrode for Loperamide.

Conditioning Solutions

Conditioning for Loperamide:

1000% peramide: 20 mg Loperamide/900 mL 0.01M HCl

100% Loperamide: 2 mg Loperamide/900 mL 0.01M HCl

Ion-Selective Electrode

The Ion-Selective electrode consists of a gradient membrane electrode specifically developed for the dissolution testing of drugs and described in H. Bohets Analytica chimica Acta 581(1):181-91, 2007 Jan. 2.

Conditioning Procedure

The concentration gradient is obtained using a dual pumping system or the gradual dilution system schematically represented in FIG. 2.

Figure 5:
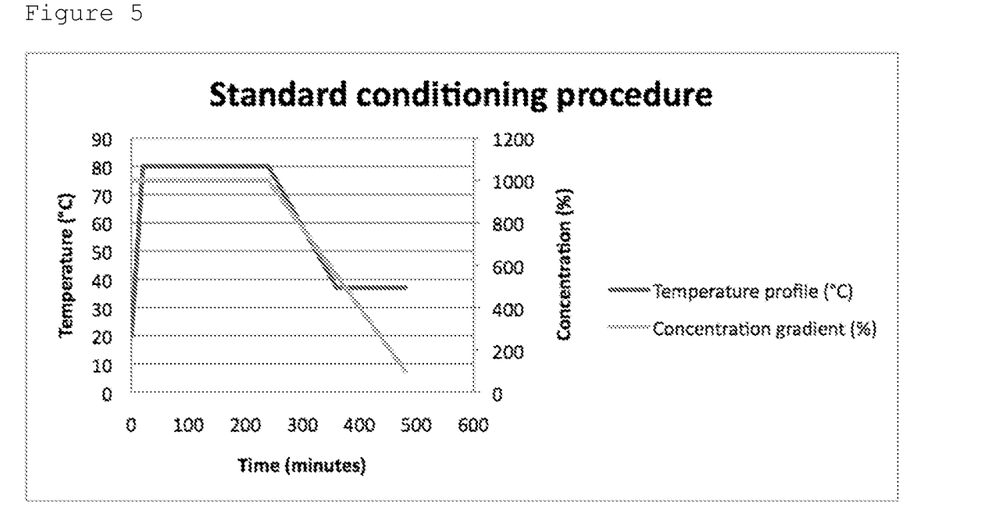
FIG. 5. Shows the temperature and concentration profile of the standard conditioning procedure with both a temperature and concentration gradient.

The conditioning process was performed using the following conditions (FIG. 5)

Conditioning temperature is kept constant at ±80° C. start with the conditioning solution at 1000% for approximately 4 h gradually converted into 100% and to 37° C. over a period of 2 h. The concentration gradient is obtained using a dual pumping system or the gradual dilution system.

Figure 6A:
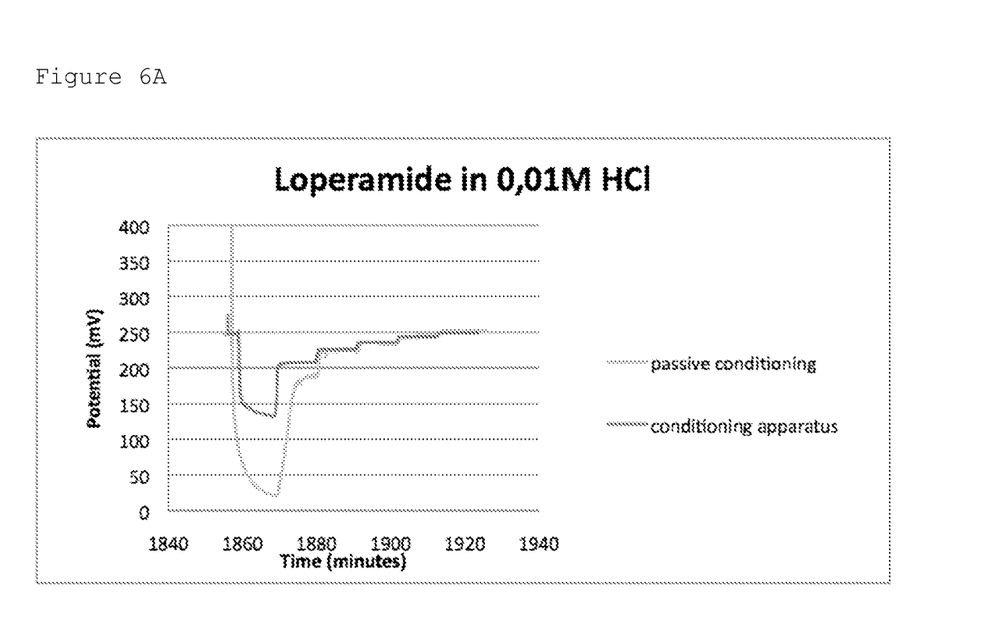
Figure 6B:
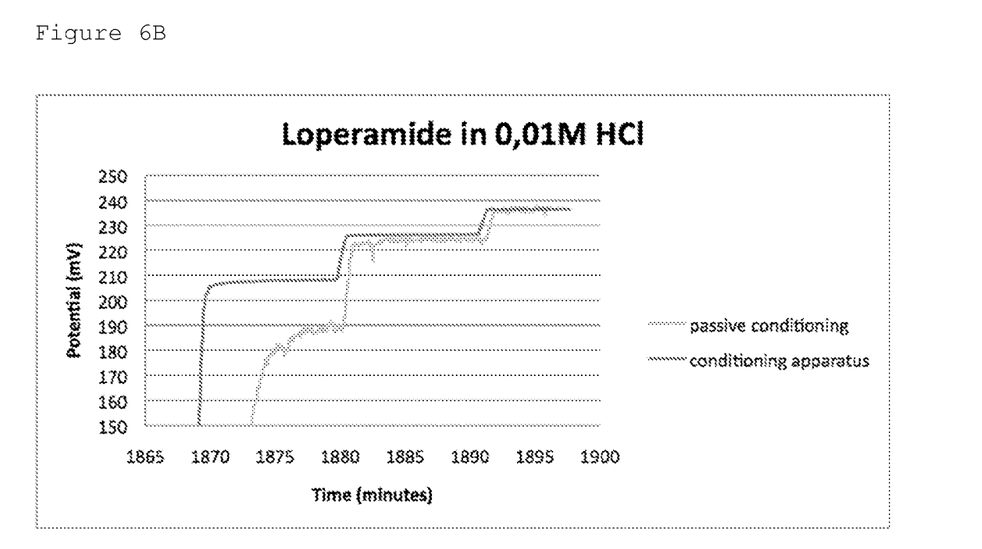

Result 120 minutes after the aforementioned conditioning procedure, measuring a 100% solution at a temperature of 37° C., the ISE yields a quick responding and full signal that is more stable than the signal of an passive conditioned electrode that had been exposed at a 100% solution for the same time range (FIG. 6A/6B), when exposed to a stepwise addition of Loperamide.

As is evident from the enlarged image in FIG. 6B the ion-selective electrode conditioned using the apparatus of the present invention shows sharp discrete steps, when compared to the noisy signal obtained using an ion-selective electrode conditioned within the same time span by passive conditioning, such as for example described in H. Bohets Analytica chimica Acta 581(1):181-91, 2007 Jan. 2.

Conclusion

From the aforementioned data it is clear that gradient-flow cell based speed-conditioning works for non-decomposing and decomposing products such as for example but not limited to ranitidine, loperamide, Cinnarizine, Amitriptyline, Diphenhydramine, and meclizinedihydrochloride.

And that post conditioning relaxation times can be reduced by choice of appropriate gradient. In addition, when compared to passive conditioned ion-selective electrodes conditioned in the same timespan, the ion-selective electrodes conditioned using the apparatus of the present invention show much better results. The electrodes showed a quick response, were more stable (less noisy signal and less drifting) and when combined with the tenside puls, were found to be less sensitive to the formation of air bubbles during measurements.

Figure 9A:
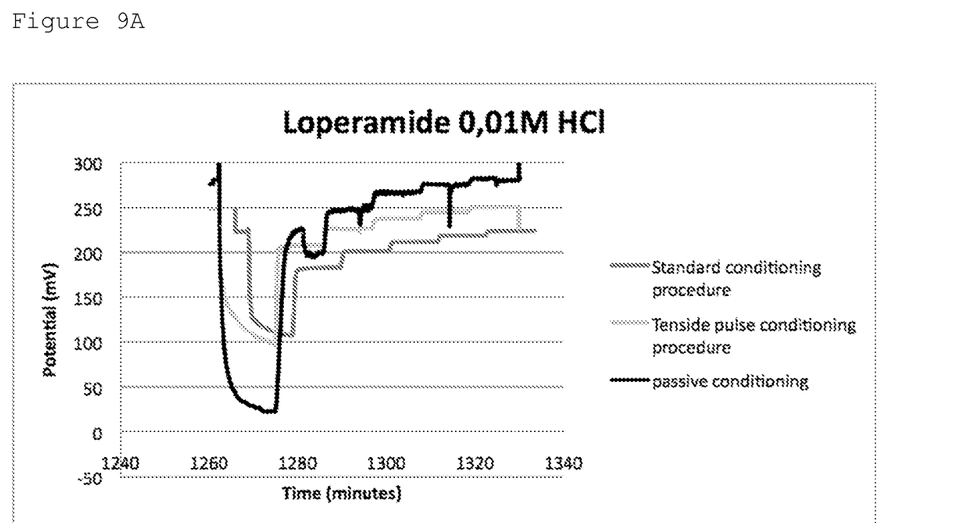
Figure 9B:
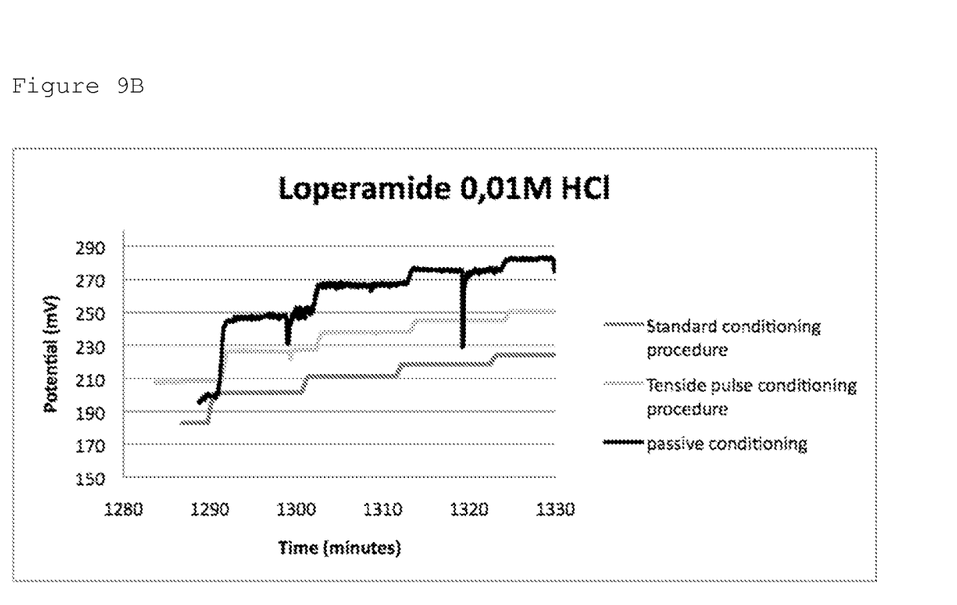

Using the condition procedures as described in example 3 (also referred to as the 'Standard conditioning procedure', or the conditioning procedures as described in example 2.2 (also referred to as the tenside pulse conditioning procedure) one obtains much faster a stable well performing electrodes than the passive conditioning such as for example described such as for example described in H. Bohets Analytica chimica Acta 581(1):181-91, 2007 Jan. 2. As shown in FIG. 9, there is no distinct difference between both 'active' conditioning methods of the present invention. Although we have to emphasizes on the fact that the tenside mechanism only requires 100% solutions as opposed to the 1000% solution for the standard conditioning procedure. Giving the tenside mechanism a distinct advantage in case of poorly soluble compounds.

Figure 10:
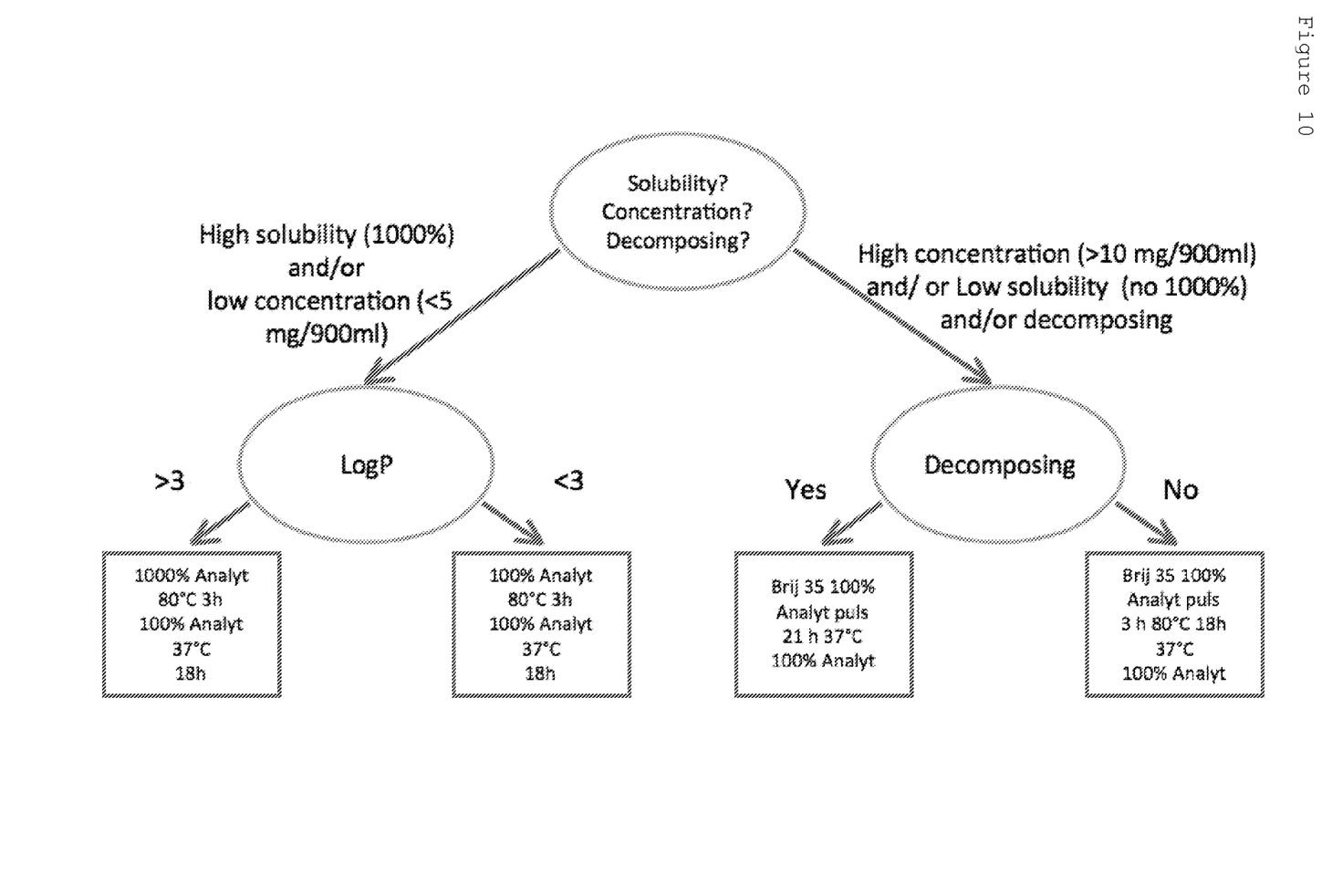
FIG. 10: Decision tree, to elect appropriate condition protocol according to the present invention.

Based on the ion of interest, and in particular the temperature sensitivity and the log P of the ion of interest, the appropriate conditioning parameters, including a temperature gradient, a concentration gradient or a combination thereof, may be determined in accordance with the decision tree shown in FIG. 10. The conditioning conditions mentioned therein, are only exemplary and not limiting for the conditioning process of the invention.

FIG. 10 depict a decision scheme based on the options of using: high or low temperature, high or low concentration and tenside. These options are selected based on the properties of the analyt of interest. Temperature sensitive products are best done at low temperature. Analytes measured at low concentration are best conditioned at high concentration (1000%). Low log P's are best conditioned at 100%. The addition of tensides is favourable in most cases but especially useful for decomposing and poorly soluble analyst.

The invention claimed is:

1. An apparatus for conditioning a universal ion selective electrode (ISE) comprising a flow through chamber capable of accommodating and contacting the ISE with a conditioning solution, wherein the ISE is conditioned via contact with a flow of the conditioning solution, and wherein said conditioning solution is applied at an elevated temperature and/or with a concentration gradient of the conditioning solution, the apparatus further comprising a water bath or other means to heat the flow through chamber and conditioning solution and maintain said flow through chamber at a desired temperature.

2. The apparatus according to claim 1, further comprising an ultrasound source to generate ultrasonic waves or mixing means to generate mechanical agitation within the flow through chamber.

3. The apparatus according to claim 1, wherein the flow through chamber is made of an inert material, free of sharp edges, of a small volume and allows easy removal of air.

4. The apparatus according to claim 1, further comprising at least one entrance feeding the flow through chamber with new conditioning solution and one exit clearing the conditioning solution after it has been in contact with the ISE.

5. The apparatus according to claim 1, further comprising a gradient pump or other means to deliver solution to achieve and control the concentration of the conditioning solution.

6. The apparatus according to claim 1, comprising:
a block heater or proportional integral derivative controller to control the temperature of the conditioning solution; and
a gradient pump or other means to deliver solution to achieve and control the concentration of the conditioning solution in the flow through chamber.

7. The apparatus according to claim 1, further comprising means to monitor the ISE at any stage of the conditioning procedure selected from means to determine one or more of the drift of an ISE signal, the flow speed behaviour of the ISE signal, or the behaviour of the ISE upon concentration variations in an ion of interest.

8. The apparatus according to claim 1, further comprising means to apply a constant or oscillating potential on the ISE electrode.

9. A method for using the apparatus of claim 1, comprising conditioning the universal ion selective electrode and monitoring a potential of the ISE at any stage of the conditioning process.

10. The method according to claim 9, wherein the conditioning process is monitored by determining a flow speed behavior of an ISE signal.

11. The method according to claim 9, wherein the conditioning process is monitored by determining a drift of an ISE signal.

12. The method according to claim 9, wherein the conditioning process is monitored by determining the behavior upon concentration variation of the ISE to validate and or calibrate the ISE electrode.

13. A method of conditioning a universal ion selective electrode with the apparatus of claim 1, said method comprising contacting said ion-selective electrode with a flow of conditioning solution in the flow through chamber of the apparatus, wherein said conditioning solution is applied at an elevated temperature and/or with a concentration gradient of the conditioning solution, the method further comprising a gradual decrease in temperature of the conditioning solution via the water bath or other means of the apparatus.

14. The method according to claim 13, wherein the concentration gradient of the conditioning solution is a variation in the concentration of one, two, three or more of the components of said conditioning solution, wherein said components are selected from the group consisting of an analyte, buffer, electrolyte, tensides, solubility promoting agents, and phase transfer catalysts.

15. The method according to claim 13, wherein the concentration gradient of the conditioning solution is a gradient in the concentration of an analyte of interest, and/or a gradient in the concentration of a background electrolyte/buffer.

16. The method according to claim 13, wherein the concentration gradient of the conditioning solution is a gradient in the concentration of an analyte of interest with a pulse in the concentration of tenside(s).

17. The method according to claim 13 wherein the concentration gradient of the conditioning solution includes a decreasing concentration of the conditioning solution.

18. The method according to claim 13, wherein the concentration gradient of the conditioning solution is a pulse in the concentration of tenside(s).

19. The method according to claim 17, wherein the concentration is decreased in a discontinuous or with a continuous gradient.

20. The method according to claim 13 wherein the temperature is continuously or discontinuously decreased.

21. The method according to claim 13, wherein heating of the conditioning solution is a flash treatment just prior to or during its exposure to the ion-selective electrode.

* * * * *

UNITED STATES PATENT AND TRADEMARK OFFICE
CERTIFICATE OF CORRECTION

PATENT NO. : 9,645,107 B2
APPLICATION NO. : 13/583267
DATED : May 9, 2017
INVENTOR(S) : Hugo Bohets It is certified that error appears in the above-identified patent and that said Letters Patent is hereby corrected as shown below:

On the Title Page

Item (57):
"ABSTRACT
Ion-selective electrodes (ISE's) optimized for analyte determinations and provides methods and apparatus for conditioning ion selective electrodes. The conditioning methods and apparatus are particularly useful for ISE's selective for, difficult to condition, less stable and temperature sensitive products, an are based on a concentration gradient and/or a short exposure to an increased temperature."
Should read:
--ABSTRACT
Ion-selective electrodes (ISE's) optimized for analyte determinations and provides methods and apparatus for conditioning ion selective electrodes. The conditioning methods and apparatus are particularly useful for ISE's selective for, difficult to condition, less stable and temperature sensitive products, and are based on a concentration gradient and/or a short exposure to an increased temperature.--;

In the Specification

Column 1, Line 30:
"etrate the boundary between two phases, then a electro-"
Should read:
--etrate the boundary between two phases, then an electro- --;

Column 2, Line 23:
"relaxation of the ISE in an analyt solution (typically 100%)"
Should read:
--relaxation of the ISE in an analyte solution (typically 100%)--;

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,645,107 B2

Column 2, Line 48:
"most useful and readily description of the principles and"
Should read:
--most useful and ready description of the principles and--;

Column 3, Line 56:
"is continuously or intermittent refreshed at the sensor sur-"
Should read:
--is continuously or intermittently refreshed at the sensor sur- --;

Column 4, Line 21:
"flow chamber, and/or by agitation of the condition solution"
Should read:
--flow chamber, and/or by agitation of the conditioning solution--;

Column 4, Line 65:
"point of the senor conditioning, its calibration, and its"
Should read:
--point of the sensor conditioning, its calibration, and its--;

Column 5, Line 34:
"concentration of the analyt (i.e. the ion/analyte of interest)"
Should read:
--concentration of the analyte (i.e. the ion/analyte of interest)--;

Column 5, Line 62:
"sisting of; the analyt, buffer, electrolyte, tensides, solubility"
Should read:
--sisting of; the analyte, buffer, electrolyte, tensides, solubility--;

Column 6, Line 14:
"gradient of the analyte (i.e. ion/analyte of interest) with."
Should read:
--gradient of the analyte (i.e. ion/analyte of interest).--;

Column 7, Line 17:
"gradually decrease in temperature and concentration of the"
Should read:
--gradual decrease in temperature and concentration of the--;

Column 7, Line 46:
"analyt to the high temperature. This together with the"
Should read:
--analyte to the high temperature. This together with the--;

Column 7, Lines 49-50:
"concentration additive profile (e.g. tensides)) was found to result in results in ISE's that are (almost) immediately"
Should read:
--concentration additive profile (e.g. tensides) was found to result in results in ISEs that are (almost) immediately--;

Column 8, Line 24:
"sensor is moved in and out the solution by varying (decrease"
Should read:
--sensor is moved in and out of the solution by varying (decrease--;

Column 8, Line 63:
"Guide to Ion-Selective Electrod Measurements"—Chris C"
Should read:
--Guide to Ion-Selective Electrode Measurements"—Chris C--;

Column 11, Line 24:
"more stable than the signal of an passive conditioned elec-"
Should read:
--more stable than the signal of a passive conditioned elec- --;

Column 12, Line 25:
"Conditioning temperature is kept constant at ±80° C. start"
Should read:
--Conditioning temperature is kept constant at ±80° C. starting--;

Column 12, Line 35:
"more stable than the signal of an passive conditioned elec-"
Should read:
--more stable than the signal of a passive conditioned elec- --;

Column 13, Line 1:
"such as for example described in H. Bohets Analytica"
Should read:
--in H. Bohets Analytica--;

Column 13, Line 5:
"have to emphasizes on the fact that the tenside mechanism"
Should read:
--have to emphasize the fact that the tenside mechanism--;

Column 13, Line 7:
"solution for the standard conditioning procedure. Giving the"
Should read:
--solution for the standard conditioning procedure, giving the--;

Column 13, Line 18:
"FIG. 10 depict a decision scheme based on the options of"
Should read:
--FIG. 10 depicts a decision scheme based on the options of--;

Column 13, Line 21:
"erties of the analyt of interest. Temperature sensitive prod-"
Should read:
--erties of the analyte of interest. Temperature sensitive prod- --; and Column 13, Line 24:
"(1000%). Low log P's are best conditioned at 100%. The"
Should read:
--(1000%). Low log Ps are best conditioned at 100%. The--.